(12) United States Patent
Genau et al.

(10) Patent No.: US 8,747,425 B2
(45) Date of Patent: Jun. 10, 2014

(54) PERCUTANEOUS VEIN REMOVAL DEVICE

(75) Inventors: Chris Genau, Seattle, WA (US); Edward M. Boyle, Bend, OR (US); Andrew Jones, Bend, OR (US); John F. Harris, Medina, WA (US); Andrew D. Firlik, Darien, CT (US); Navroze S. Mehta, Boca Raton, FL (US)

(73) Assignee: VenX, LLC, Nashville, TN (US)

( * ) Notice: Subject to any disclaimer, the term of this patent is extended or adjusted under 35 U.S.C. 154(b) by 0 days.

(21) Appl. No.: 13/462,988

(22) Filed: May 3, 2012

(65) Prior Publication Data
US 2013/0123819 A1     May 16, 2013

Related U.S. Application Data

(63) Continuation-in-part of application No. 12/766,165, filed on Apr. 23, 2010.

(60) Provisional application No. 61/483,875, filed on May 9, 2011.

(51) Int. Cl.
*A61B 17/32*     (2006.01)

(52) U.S. Cl.
USPC ............................ 606/170; 606/159; 606/185

(58) Field of Classification Search
USPC ......... 606/108, 138, 139, 144–147, 159, 167, 606/170, 180, 185, 186, 190, 205, 210; 604/46, 164.01, 264; 81/442–447; 600/131, 141, 142, 146
See application file for complete search history.

(56) References Cited

U.S. PATENT DOCUMENTS

| | | | | |
|---|---|---|---|---|
| 3,638,654 A | * | 2/1972 | Akuba | 606/144 |
| 5,282,806 A | | 2/1994 | Haber et al. | |
| 5,545,148 A | | 8/1996 | Wurster | |
| 5,722,990 A | | 3/1998 | Sugarbaker et al. | |
| 5,782,844 A | * | 7/1998 | Yoon et al. | 606/139 |
| 5,830,221 A | * | 11/1998 | Stein et al. | 606/157 |
| 6,126,665 A | | 10/2000 | Yoon | |
| 6,224,618 B1 | | 5/2001 | Gordon | |

* cited by examiner

*Primary Examiner* — Kathleen Holwerda
*Assistant Examiner* — Sarah W Aleman
(74) *Attorney, Agent, or Firm* — Stites & Harbison PLLC; Manydy Wilson Decker; James Hayne

(57) ABSTRACT

A surgical tool for the obliteration of spider veins.

3 Claims, 7 Drawing Sheets

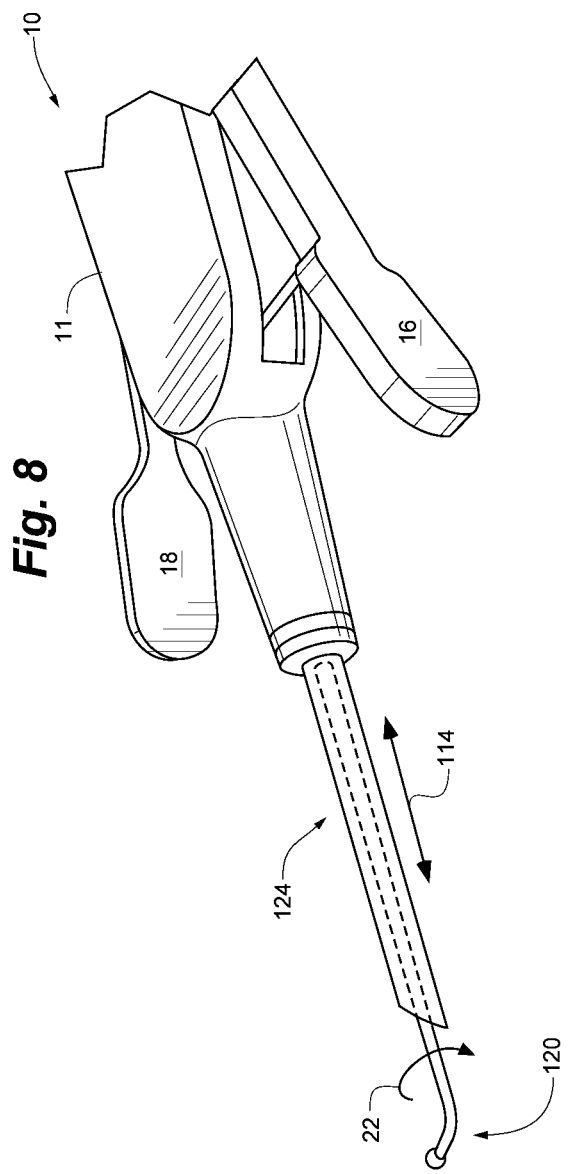

PERCUTANEOUS VEIN REMOVAL DEVICE

CROSS REFERENCE TO RELATED CASES

The present filing is a continuation in part of U.S. Utility patent application Ser. No. 12/766,165 entitled "Vein Removal Device" and further claims the benefit of U.S. Provisional Application 61/483,875 entitled "Macro-Phlebectomy Device"

FIELD OF THE INVENTION

The present invention relates generally to vein obliteration technology and more particularly to a surgical instrument operated by a physician for locating, intercepting and obliterating spider veins.

BACKGROUND OF THE INVENTION

The heart pumps blood to supply oxygen and nutrients to all parts of the body. Arteries carry blood from the heart towards the body parts, while veins carry blood from the body parts back to the heart. Veins contain one-way valves to prevent the blood from flowing backwards. If the one-way valve becomes weak, some of the blood can leak backwards through the valve, collect in the vein upstream of the valve, and then become congested as the pressure builds. This congestion will cause the vein to abnormally enlarge. These enlarged veins can be seen on the surface of the skin as either varicose veins or spider veins.

Varicose veins are swollen and raise the surface of the skin. Spider veins are similar to varicose veins, but they are smaller, are often red or blue in color, and are closer to the surface of the skin than varicose veins. They are also known as telangectasias. They can cover either a very small or very large area of skin. Spider veins are connected to larger vein systems through reticular veins. As such, spider veins aren't necessary for circulation, rather they result when high pressure in veins from faulty valves stretch out the normally small and invisible surface skin veins forming abnormally distended and visible veins. Since venous pressure is highest in the legs, spider veins are most commonly found on the lower extremities, but they can be found anywhere on the surface of the skin.

At present there are two main treatment options for spider veins: sclerotherapy and surface laser treatment.

Sclerotherapy involves injecting a sclerosing solution into the vein, causing it to shrink and fade from the surface of the skin. Having this treatment can also reduce the symptoms that are commonly associated with spider veins, including, burning, itching, cramping and swelling. With time the appearance of the spider veins fades to a variable degree. Laser therapy focuses light on the vein which preferentially absorbs the light and suffers injury.

There are a number of shortcomings of sclerotherapy to treat spider veins. Serious medical complications from sclerotherapy are relatively rare, however, they may occur. Risks include the formation of blood clots in the superficial and deep veins, which is referred to as superficial vein thrombophlebitis and deep vein thrombosis, both of which are serious medical conditions that can have severe short term and long term consequences. Some deep vein thrombosis (DVT) can break loose and can travel to the lungs (pulmonary embolism), which can be fatal. Foam sclerotherapy has reportedly caused transient ischemic attacks, suggesting that the sclerotherapy can travel to the brain and cause damage. Additionally severe inflammation and adverse allergic reactions to the sclerosing solution can occur. Occasionally, skin injury known as an ulcer, a form of skin necrosis which leaves a small but permanent scar, can occur.

In addition to these potential serious reactions, there are a number of very common outcomes to sclerotherapy that are undesirable. A common cosmetic complication is pigmentation irregularity. These are brownish splotches on the affected skin that may take months to fade, sometimes up to a year or more. This is also known as staining or shadowing. Another problem that can occur is "telangiectatic matting," in which fine reddish blood vessels appear around the treated area, sometimes requiring further injections or laser treatments to help fade the reddish discoloration. Both of these complications are thought to be related to severe and persistent inflammation that results from the chemical damage to the vein after sclerotherapy. In some cases, discoloration can persist when the hemoglobin from the damaged vein is absorbed by the skin, leaving a permanent brownish discoloration to the skin. Another problem with sclerotherapy is that the concentration and treatment effect of the sclerotherapy solution is different at different points along the vein depending on the distance from the injection site and the degree of vein branch aborization distal to the injection site. As the sclerosant travels in the vein it becomes less concentrated leading to variable zones of treatment that vary from too much to just right to too little. This effect is often undesirable to patients.

Another option is to use surface laser to treat spider veins. The energy is absorbed by the hemoglobin in the blood causing a local reaction that heats the vein and injures the endothelium and other vascular wall structures. During laser treatment, a laser is applied to the skin over the spider veins. Laser energy causes the spider veins to coagulate and shrink. Laser therapy is most effective for small and medium size spider veins because it is unable to adequately injure vessels. Most patients experience mild discomfort similar to having a small rubber band snapping against skin and treatments usually do not require sedatives, pain medications, or injections of local anesthetic. Immediately following treatment, spider veins will be darker and more visible. Over two to six weeks, a percentage of the spider veins usually fade while others persist, thus more than one treatment is necessary. Retreating the areas requires a long treatment interval because the cumulative effect can cause skin necrosis or sloughing. With both sclerotherapy and laser therapy the post treatment skin can react unfavorably to sunlight in the healing phase, leading most practitioners to caution against sun exposure either before or after treatment. Many patients seeking treatment for spider and reticular veins are doing so due to their desire to obtain sun exposure, thus limiting treatment sessions to times when patients can reliably expect to keep their veins out of the sun before or after the treatment.

Clearance is neither complete nor immediate with both sclerotherapy and surface laser, which have significant undesirable effects. In each case there is enough injury to cause a wound healing response as the vein fades away over time. Failure to clear the spider vein occurs when the injury is insufficient to the vein wall structure. In the case of sclerotherapy, this happens in the far reaches of vein from the injection site, resulting in uneven and incomplete results. With laser, this occurs when there is insufficient heat generated to damage the inside of the vein. The larger the vein, the more likely the laser to be unsuccessful in clearing the spider vein. Alternatively, sclerotherapy can result in a prolonged wound healing phase where the vein is visibly damaged, yet it takes months to become invisible as the body's inflammatory system works to clear the damaged vein through the wound healing process.

Both sclerotherapy and surface skin laser involve injuring the internal vein structure in a fashion that results in thrombosis of the vein and injury to the vein. With sclerotherapy, the injury is in the form of a chemical irritant to the internal lining of the vein, known as the endothelium. With surface laser, a focused beam of light with variable absorption characteristics is utilized to travel from the hand piece through the skin to injure the underlying vein. Vein injury triggers in a wound healing response. The wound healing response is known to include following steps: 1) Inflammation; 2) FibroProliferation; 3) Contraction and 4) Remodeling. It is generally understood that a wound will not heal until the initial inflammatory step is complete. Thus minimizing inflammation is key to the speed and completeness of treatment.

This is the problem with sclerotherapy. In sclerotherapy the degree of endothelial and sub endothelial damage is variable along the length of the treated vein, as is the degree of inflammation. Patients complain of feeling pain and heat along the treated veins for many months. Areas of entrapped coagulated blood usually associated with discolorization, all of which patients find undesirable. When this occurs, return visits are often required to puncture and drain these areas. Residual areas of entrapped, inflamed and coagulated blood persist and impact the degree of discomfort and lessen patient satisfaction. This can persist for many months and sometimes for more than a year. Most patients require multiple treatments and degree of residual discolorization and discomfort lengthen the interval between treatments. Due to these limitations, patients often choose not to continue with treatments and they are left with residual discoloration.

An alternative vein treatment method is ambulatory phlebectomy, also known as phlebectomy. Phlebectomy is a technique commonly utilized for larger diameter, branch varicose veins that are visible by bulging out of the skin when the patient is standing Phlebectomy always involves cutting the skin, fishing out the vein, and pulling on it to break or injure the vein, and then applying pressure. With this technique, the vein is marked with the patient standing, and then once the overlying skin and subcutaneous tissues are anesthetized, a small incision is made and a hook is inserted into the incision to hook the vein. Once the vein is hooked, the operator pulls the hook and vein out, snapping the vein, most often removing a small segment of vein in the process. This process is repeated, on average for 10 to 20 incisions per treatment session. The disrupted veins are then compressed in a dressing that allows the vein segments to clot off, preventing continued bleeding. Alternatively, some surgeons ligate each end of the vein so that the small vein segment can be removed without allowing the remaining segments to continue to bleed. Incision sizes range from 5 cm to 0.5 cm. Small diameter veins, such as reticular veins and spider veins are generally too small to be treated with this technique.

One problem with current ambulatory phlebectomy is that that it is difficult to find the veins when the patient is laying down for treatment. Usually the veins are marked with a permanent felt tip pen when the patient is standing. Then the patient is put in the supine or prone position for treatment. At this point, the veins become decompressed and no longer visible. When attempting to perform phlebectomy, the area to be treated is anesthesized, then a knife blade is used to incise the skin overlying the vein that was marked with a felt tip pen. A crochet hook or specially designed phlebectomy hook is put into the wound and the operator attempts to find the vein. Once the vein is found, it is pulled out of the incision and either avulsed or clamped, cut and tied. If the skin is lax and moves relative to the vein when the patient goes from the standing to laying position, the operator can be unsuccessful in finding the vein, especially if the incision in the skin is small.

An additional embodiment is endovenous treatment. With endovenous treatment, a catheter is threaded into a vein, usually under ultrasound guidance, and the catheter tip uses laser, radiofrequency or steam to damage the inside of the vessel wall. As the catheter is withdrawn, the length of the vein is treated. Ideal veins for endovenous treatment are larger diameter (usually 3 mm to 20 mm), relatively straight (because curving veins cannot be cannulated as successfully), and remote from the surface of the skin (because the skin can be burned if the vein is too near the skin, resulting in significantly increased pain and discoloration). Thus this is usually reserved for the great and small saphenous veins, and occasionally, larger straighter incompetent perforator veins. Disadvantages of endovenous therapy include the limitations on the type of veins (larger, straight, deeper) that can be treated. Furthermore, the degree of damage surrounding the vein is variable, ranging from too little (and thus failed treatment) to too severe, leading to pain and collateral damage to other vessels and nerves. One device used to treat spider veins is described in U.S. Pat. No. 6,224,618 to Gordon. Gordon teaches a handheld device that consists of a sharp trocar-like tip divided into two tines for straddling a vein and permitting the physician to cut the vein by rotating the instrument. Although this technique and device have proved successful there is a continuing need for improved spider vein obliteration tools.

SUMMARY OF THE INVENTION

The present invention relates generally to a tool that can be used conveniently by a physician or other user to intercept and rotate a spider vein or other vein. In contrast to prior art devices that simply cut the vein the present device includes two tines that in use straddle the spider vein with blunt, non-cutting surfaces. Rotation of the tool supplies force to the vein and the tissues surrounding the vein. The tool is rotated enough to disrupt the vein and create an extensive injury to the vein and the immediate tissue at the site of the intervention. This form of injury prevents the vein from re-cannulizing and therefore results in vein obliteration. The applicants have discovered that this distributed injury results in the more reliable removal of the spider vein than the previously known vein cutting technique.

BRIEF DESCRIPTION OF THE DRAWINGS

Throughout the figures of the drawing identical reference numerals indicate identical structure, wherein:

FIG. 8 shows a perspective view of an alternate embodiment of the device.

DETAILED DESCRIPTION OF THE INVENTION

Figure 1:
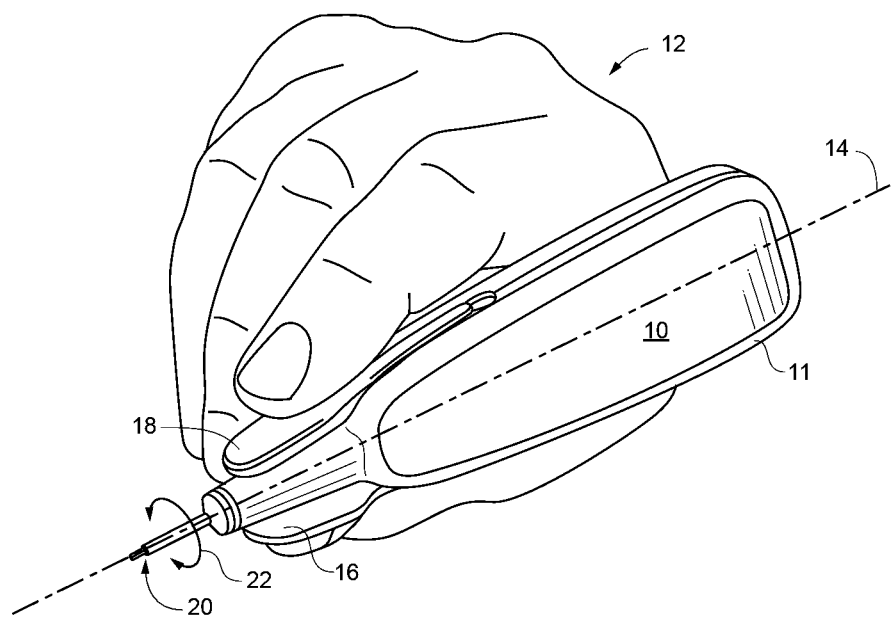
FIG. 1 shows the device in the hand of a physician user.

FIG. 1 shows the device 10 resting in the hands of a physician 12. The device lies in the hand between the thumb and forefinger. The device has an elongate axis 14 and a set of finger paddle levers typified by lever arm 16 and lever arm 18 for activation by the physician's fingers. The physician squeezes the two lever arms together to activate the device. The energy supplied by translating the motion of the physicians fingers causes rotation of the distal tip assembly 20 about the axis 14 as indicated by motion arrow 22. The total or maximum amount of rotation is controlled by the design of the device. If the physician limits depression of the finger paddles he may reduce the amount of rotation of the distal tined tip. The distal tip assembly 20 includes two pointed tines 30 and 32 that are each generally cylindrical in cross-section. The axis of the two tines are parallel to each other over much of their length and are robust in construction such that they maintain positional alignment with respect to each other during use. In use the physician locates a spider vein and uses the device 10 to injure and therefore disrupt the spider vein.

Figure 2:
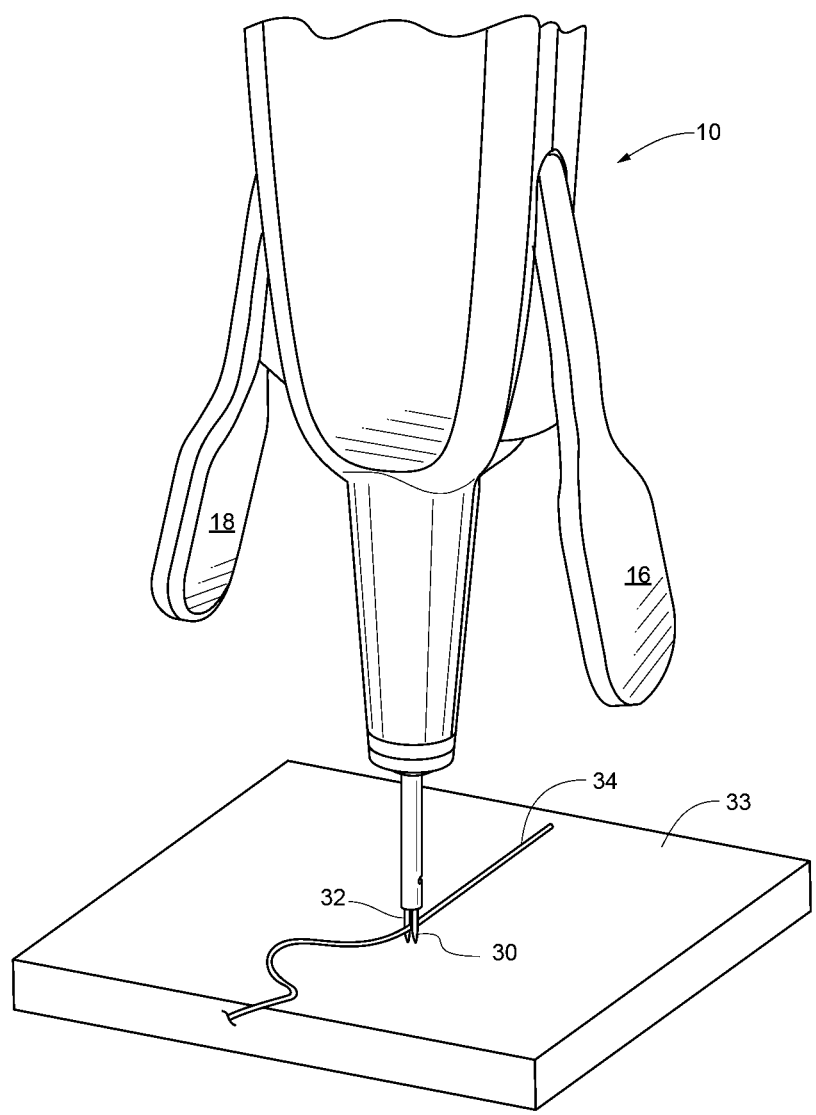
FIG. 2 shows the device interacting with a vein and related tissue.
Figure 3:
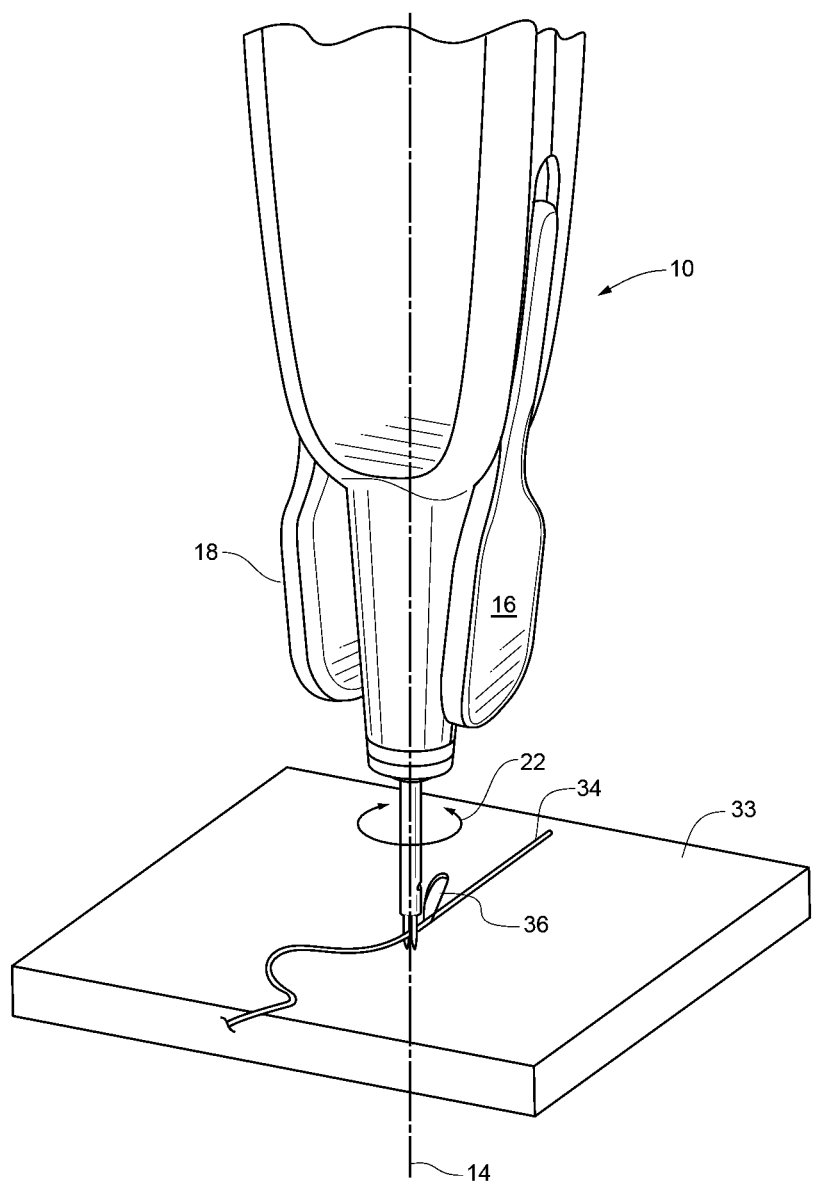
FIG. 3 shows the device interacting with the tissue.

FIG. 2 shows this interaction of the device 10 with tissue 33. The physician plunges the tip 20 into the skin and maneuvers it such that the tines 30 and 32 straddle the vein 34. The physician can then squeeze the lever arms together. The lever arms move from an initial position with the levers away from the body of the tool as depicted in FIG. 2 to an end position with the levers alongside the body of the device as depicted in FIG. 3. This squeezing action rotates the tine assembly about axis 14. A successful disruption may be indicated by a blood droplet 36 (FIG. 3) emerging from the wound. The physician will next remove the device from the wound and let the lever arms recoil to the initial position, ready for use at the next site.

Full compression of the levers moves the device from a static initial state or position to a competed location with the tip fully rotated a selected number of degrees in the tissue. Due to the elasticity of skin and the relatively coupled relationship of spider vein to surrounding tissue, the optimal amount of rotation required is believed to be about 270-360 degrees from the initial position to the completion position. Experiment has shown that the tissue trapped between the tines must be completely insulted to permanently disrupt the vein. The physician may feel a graduated increase in resistance as he rotates the distal tip assembly in the wound. Finally the tissue trapped between the tines tears and a drop of blood emerges from the puncture in the skin. At this point the physician may stop pressing the lever arms if there is still some travel available, or he may continue to the completed position of the device. The blood droplet indicates successful vein disruption and it usually occurs between 270 and 360 degrees of rotation around axis 14.

Figure 4:
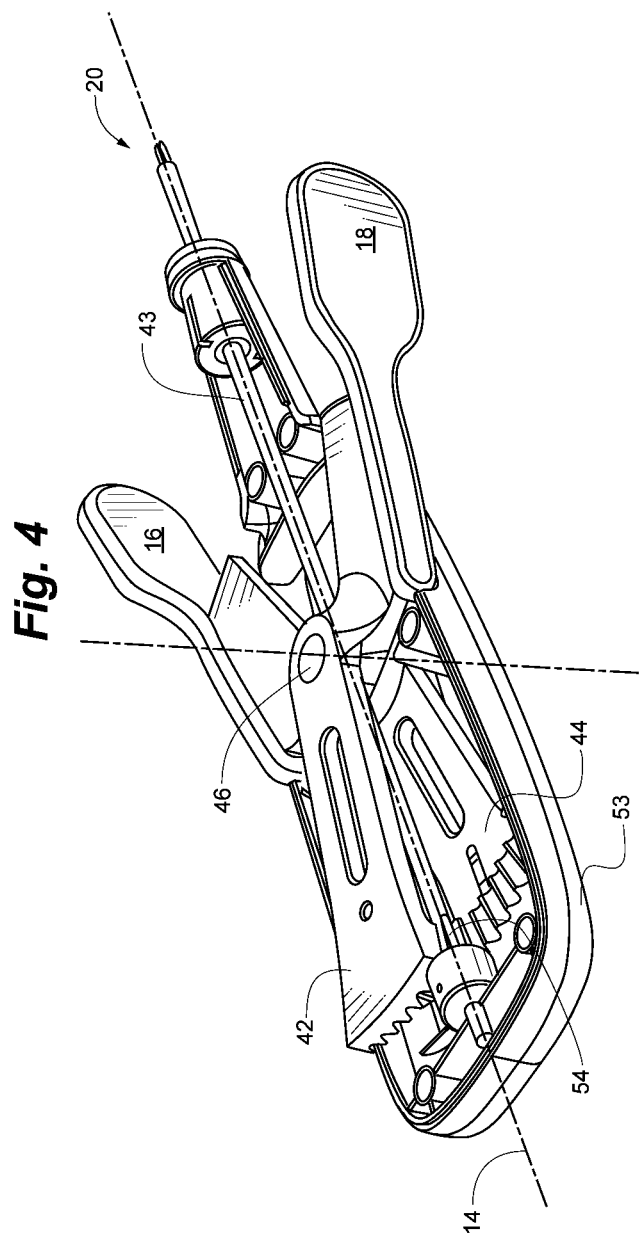
FIG. 4 shows a perspective view of the device.

FIG. 4 shows a perspective view of the interior of the device 10 and shows one embodiment of a mechanical gearing arrangement for translating the surgeon's squeezing of the paddle lever arms to a rotational movement of the tip. Each finger paddle lever 16 and 18 forms a sector gear within the housing. The sector gear for lever arm 18 is labeled 42 in the figure. The complimentary sector gear 44 is formed integrally with lever arm 16. Both finger lever arms share a common axis of rotation or common axle 46. Both arms are mounted for pivoting around this common axle 46 that is perpendicular to axis 14. The finger lever arms and associated sector gear segments are biased against each other by a wound torsion spring 48, shown in FIG. 5. The housing or body 53 shown is half of a clam shell construction the forms the body 11 of the device 10.

Figure 5:
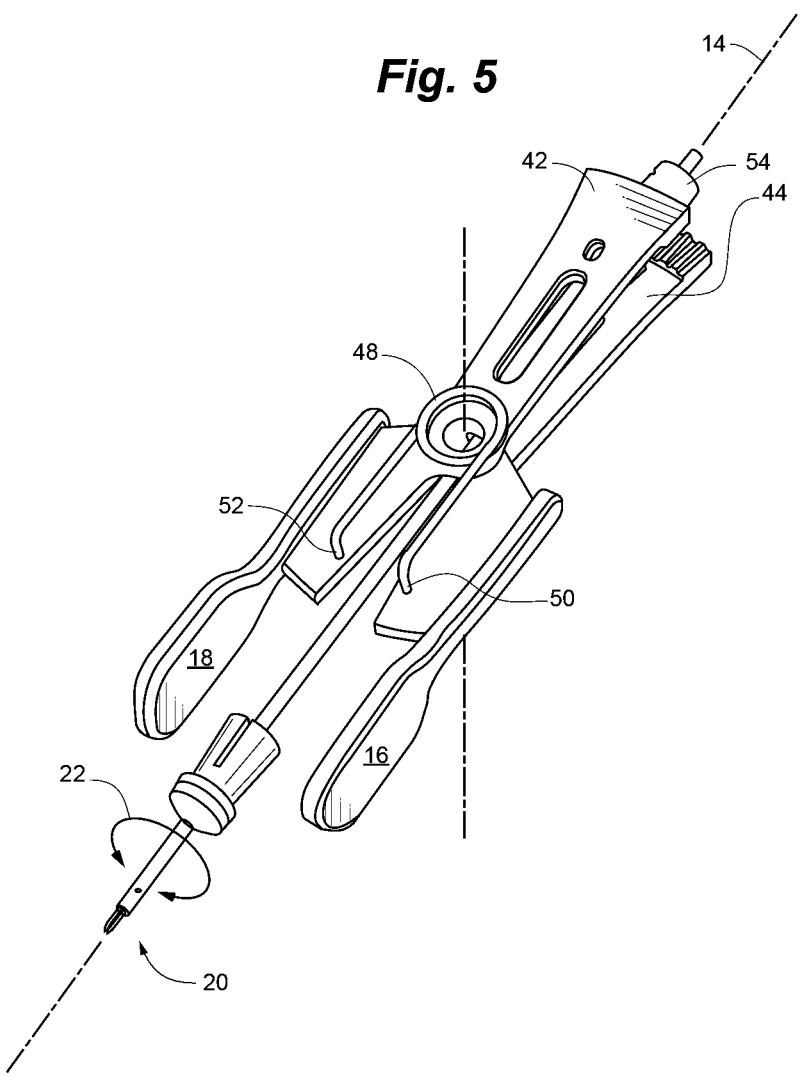
FIG. 5 shows a perspective view of a portion of the device.

FIG. 5 shows a portion of the mechanism in isolation to improve clarity of operation. As seen in FIG. 5 the spring 48 is anchored in both lever arm 16 and 18 at locations 50 and 52. This arrangement causes the lever arms to react against each other to improve the "feel" or sensitivity of the device. It is believed that the haptics of the device will be important to its acceptance and use. As the two gear sectors scissor past each they drive a pinion gear 54 rotating about axis 14. This pinion gear 54 is coupled to shaft 43 that connects to the tip assembly 20. The pinion gear 54 and shaft 43 are journaled in bearings not labeled that serve to retain the shaft within the housing or body while still allowing smooth rotation. The pinion gear 54 further serves to keep the levers mechanically mated to each other in synchronous fashion such that pivoting or actuating movement of one lever is dependent on movement of the second lever. In summary lever motion results in rotation of the tine assembly 20 and a restoring force supplied by spring returns the levers to the initial position.

The sector gear tooth count and pitch to pinion diameter pitch and tooth count establish a ratio that is selected to provide the maximum desired amount of rotation, for example 360 degrees in a size that is acceptable to most users hands.

Figure 6:
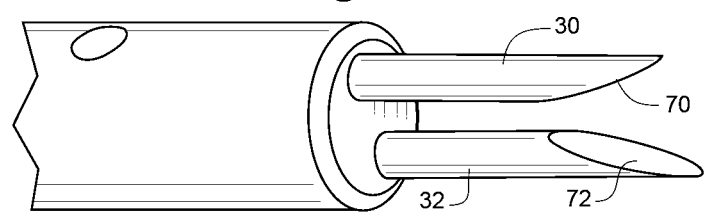
FIG. 6 shows a perspective view of an embodiment of the tip of the device.

FIG. 6 shows one configuration of the tip assembly 20 with two cylindrical tines terminating in elliptical tissue piercing tips (created via angle grind) identified in the drawing at 70 and 72 respectively.

Figure 7:
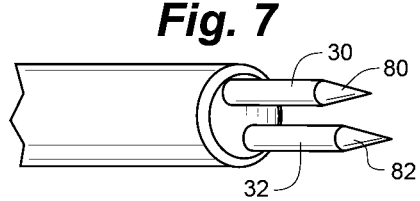
FIG. 7 shows a perspective view of an embodiment of the tip of the device.

FIG. 7 shows an alternate distal tip assembly 20 configuration wherein the two cylindrical tines 30 and 32 are terminated in conical tips shown as 80 and 82 respectively.

The tines are generally parallel to each other to ease entry into the tissue and to not cause undue damage to tissue.

FIG. 8 shows an alternative version of the device. In this embodiment the parallel tines are supplanted by a hook structure that is similar in form to the so-called Mueller hook used in open surgery. The device 10 has an instrument body 11 that is held in a physician's hand. His fingers may operate a pair of opposed levers 16, 18. When pressed the levers rotate 22 a hooked needle 120. As a part of the treatment the handle 11 may be retracted with the hook 120 engaging a vein as indicated by motion arrow 114. To permit entry into the skin a hypodermic needle 124 may be included in the assembly to allow entry into the dermal layers by motion along path 114. Alternatively a mechanism not shown may advance the hypodermic needle into the skin. In either case the hypodermic needle will cover the needle 120 during entry into the skin. The needle will emerge from the assembly and hook the vein. Rotation and retraction will disrupt the vein.

The device is intended to be a single use tool however reusable versions are contemplated within the scope of the invention. It is proposed to have single tip configuration but a replaceable tip is contemplated within the scope of the invention.

Many alterations of the invention are possible without departing from the scope of the claims.

What is claimed is:

1. A surgical tool for obliterating a vein comprising:
   a stationary body adapted to be held and manipulated by a hand;
   a first lever arm adapted to be actuated by a finger;
   a second lever arm adapted to be actuated by a finger;
   said first and second lever arms are external to and on opposing sides of said body;
   an axle passing through said first and second lever arms forming a pivot for each lever arm and anchoring the lever arms in said body;
   a first gear sector coupled to said first lever arm;
   a second gear sector coupled to said second lever arm;
   a pinion gear meshed with each gear sector to translate motion of the lever arms into a rotational motion of a pinion shaft;
   a tip assembly coupled to said shaft;

said tip assembly having a hook with blunt surfaces adapted to capture a vein;

whereby lever arm motion about the pivot rotates the tip assembly obliterating the vein by mechanical trauma, wherein a squeezing lever arm motion from an initial position to an end position rotates the tip assembly in a first direction, and a returning lever arm motion from the end position to the initial position rotates the tip assembly in a second direction opposite the first direction.

2. The surgical tool of claim 1, wherein an intermediate position of the lever arm is located between the initial position and the end position, such that the lever arms may move from the initial position to the intermediate position and return to the initial position without ever being in the end position.

3. A surgical tool for obliterating a vein comprising:
a stationary body adapted to be held and manipulated by a hand;
a first lever arm adapted to be actuated by a finger;
a second lever arm adapted to be actuated by a finger;
said first and second lever arms are external to and on opposing sides of said body;
an axle passing through said first and second lever arms forming a pivot for each lever arm and anchoring the lever arms in said body;
a first gear sector coupled to said first lever arm;
a second gear sector coupled to said second lever arm;
a pinion gear meshed with each gear sector to translate motion of the lever arms into a rotational motion of a pinion shaft;
a tip assembly coupled to said shaft;
said tip assembly having a hook with blunt surfaces adapted to capture a vein;
whereby lever arm motion about the pivot rotates the tip assembly obliterating the vein by mechanical trauma, wherein the tip assembly further comprises a hypodermic needle such that the hook is contained within the hypodermic needle when the tip assembly is in an entry configuration, and the hook is exterior to the hypodermic needle when the tip assembly is in an operational configuration.

* * * * *